United States Patent [19]

Jessel, Jr. et al.

[11] Plant 4,156

[45] Nov. 22, 1977

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 743,060

[22] Filed: Nov. 18, 1976

[51] Int. Cl.[2] ..... A01H 5/00

[52] U.S. Cl. ..... Plt./74

[58] Field of Search ..... Plt./74

*Primary Examiner*—Robert E. Bagwill
*Attorney, Agent, or Firm*—Donald D. Jeffery

[57] ABSTRACT

This invention relates to a novel chrysanthemum characterized by its spooned daisy inflorescence form and yellow-bronze ray florets.

3 Drawing Figures

1

The present invention comprises a new and distinct cultivar of *Chrysanthemum morifolium,* Ramat., hereinafter referred to by the cultivar name Jamboree (No. 73116022).

Jamboree is a product of a planned breeding program which had the objective of creating new cultivars of *Chrysanthemum morifolium,* Ramat. for use as cut sprays with spooned daisy inflorescence type, with pink and bronze inflorescence color, with nine week photoperiodic flowering response, and with high gradeout (Society of American Florist standards). Such traits in combination were not present in previously available commercial cultivars.

Jamboree was originated from a cross made in a controlled breeding program in Barberton, Ohio in 1972. The female, or seed parent, was No. 70025007 (unnamed seedling) a white spooned daisy originated by the present inventors from a cross between No. 66026001 (unnamed seedling) and Illini Spinwheel (No. 21670E02; U. S. Plant Pat. No. 3,379). The male, or pollen parent, of Jamboree was Neptune (No. 60228002; unpatented; commercially available), a white decorative originated by the present inventors from a cross between Ice Follies (No. 55372004; unpatented; commercially available) and No. 54972002 (unnamed seedling). Ice Follies, No. 66026001, and No. 5472002 are products of the breeding program of the present inventors. Illini Spinwheel is of parentage unknown to the present inventors.

Jamboree was discovered and selected as a flowering plant within the progeny of the stated cross by Walter H. Jessel, Jr. and William E. Duffett on Apr. 4, 1973 in a controlled environment in Barberton, Ohio.

The first act of asexual reproduction of Jamboree was accomplished when vegetative cuttings were taken from the initial selection in June, 1973 in a controlled environment in Barberton, Ohio by a technician working under formulations established and supervised by Walter H. Jessel, Jr. and William E. Duffett. Horticultural examination of selected units initiated May 21, 1975 has demonstrated that the combination of characteristics as herein disclosed for Jamboree are firmly fixed and are retained through successive generations of asexual reproduction.

Jamboree has not been observed under all possible

2 environmental conditions. The phenotype may vary significantly with variations in environment such as temperature, light intensity and daylength. The following observations, measurements, and comparisons describe plants grown in Barberton, Ohio under greenhouse conditions which approximate those generally used in commercial practice, as described in Chart A which appears at the end of the present specification. A light intensity chart of general use is shown in FIG. 14.14 in ASHAE Trans., Vol. 64, pg. 64, and reference is made thereto.

The following traits have been repeatedly observed and are determined to be basic characteristics of Jamboree which in combination distinguish this chrysanthemum as a new and distinct cultivar:

1. Spooned daisy inflorescence type.
2. Flat inflorescence form.
3. Orange-bronze to yellow-bronze ray floret color.
4. Medium green disc floret color at immature, unopened stage.
5. Diameter across face of inflorescence up to 110 mm. at maturity.
6. Uniform nine week photoperiodic flowering response to short day control.
7. Medium plant height (requires 1–2 long day weeks prior to short days to produce 72 to 82 cm. height when grown as a single stem plant from May through October).
9. Minimal pollen development.

The accompanying photographic drawings show typical inflorescence and foliage characteristics of Jamboree. Sheet 1 is a color photograph of Jamboree. Sheet 2 is a black and white photograph showing three views of the inflorescence of Jamboree. Sheet 3 is a black and white photograph of the foliage of Jamboree at three stages of growth.

Of the many commercial cultivars known to the present inventors, the most similar existing cultivar in comparison to Jamboree is Dramatic (No. 67079001; U.S. Plant Pat. No. 3,189). Reference is made to attached Chart B which compares certain characteristics of Dramatic with the same characteristics of Jamboree. In comparison to Dramatic, Jamboree has different inflorescence color, different inflorescence type, and larger diameter across face of inflorescence. The inflorescence form, plant height, and flowering response of Jamboree are similar to those of Dramatic.

In the following description, color references are made to The Munsell Limit Color Cascade, 1972 edition. The color values were determined between 9:00 and 9:30 on May 5, 1976 under 200 foot-candle light intensity at Barberton, Ohio.

Botanical classification: *Chrysanthemum morifolium,* Ramat., cv. Jamboree.

Reproductive organs:

*Androecium.*—Numerous; scant pollen.

*Gynoecium.*—Present both ray and disc florets.

PLANT

General appearance: semi-upright, medium height.

Foliage (see Sheets 1 and 3 of drawings):

*Color (abaxial).*—21-15.

*Color (adaxial).*—21-14.

CHART A
AVERAGE GREENHOUSE CHRYSANTHEMUM ENVIRONMENTS USED FOR BARBERTON, OHIO

| SEASON | TEMPERATURES USED Night | Bright Day | Cloudy Day | LIGHTING USED | BLACK CLOTH USED | SUPP $CO_2$ |
|---|---|---|---|---|---|---|
| FALL | 65° F to | 65° F to | 60° F to | 2 to 4 weeks at 3 Hours Per Night of 7–10 f.c. | To Sept. 15 on - 5:30 PM Off-7:30 AM | From Oct. 15 300 ppm |
| WINTER | 56° F 58° F to | 80° F 65° F to | 75° F 60° F to | 2 to 5 weeks at 5 hours Per Night of 7–10 f.c. | NONE | 300 ppm |
| SPRING | 62° F 58° F to | 70° F 65° F to | 65° F 60° F to | 2 to 4 weeks at 5 Hours Per Night of 7–10 f.c. | From Mar. 15 on - 5:30 PM Off-7:30 AM | To Apr. 15 300 ppm |
| SUMMER | 65° F 62° F to 68° F | 80° F 70° F to 90° F | 75° F 65° F to 75° F | 1 to 2 weeks at 3 Hours Per of 7–10 f.c. | on-6:00 PM Off-8:00 AM | NONE |

CHART B — COMPARISON OF JAMBOREE AND DRAMATIC

| CULTIVAR | RAY FLORET COLOR | INFLORESCENCE FORM AND TYPE | PLANT HEIGHT | FLOWERING RESPONSE PERIOD | DIAMETER ACROSS FACE OF INFLORESCENCE |
|---|---|---|---|---|---|
| Jamboree | Orange Bronze to Yellow Bronze | Flat Spooned Daisy | Medium | 9 week | 90 to 110 mm. |
| Dramatic | Golden Bronze to Yellow | Flat Daisy | Medium | 9 week | 75 to 100 mm. |

COMPARISONS MADE OF PLANTS GROWN IN A GREENHOUSE IN BARBERTON, OHIO UNDER CONDITIONS DESCRIBED IN CHART A.

INFLORESCENCE

Capitulum (see Sheets 1 and 2 of the drawings):

*Form.*—Flat.

*Type.*—Spooned daisy.

*Permanence.*—14 to 21 days.

*Diameter across face.*—90 to 110 mm.

Corolla of ray florets (see Sheets 1 and 2 of drawings):

*Color (abaxial).*—30-12 to 29-11 over 27-9.

*Color (adaxial).*—28-12 over 27-4.

Corolla of disc florets (see Sheets 1 and 2 of drawings)

*Color:* 22-12 (immature) to 28-9 (mature).

We claim:

1. A new and distinct cultivar of *Chrysanthemum morifolium,* Ramat., plant known by the cultivar name Jamboree and particularly characterized as to uniqueness by the combined characteristics of spooned daisy inflorescence type; flat inflorescence form; orange-bronze to yellow-bronze ray floret color; medium green disc floret color at immature, unopened state; diameter across face of inflorescence up to 110 mm. at maturity; uniform nine week photoperiodic flowering response to short day control; medium plant height; semi-upright branching pattern, and minimal pollen development.

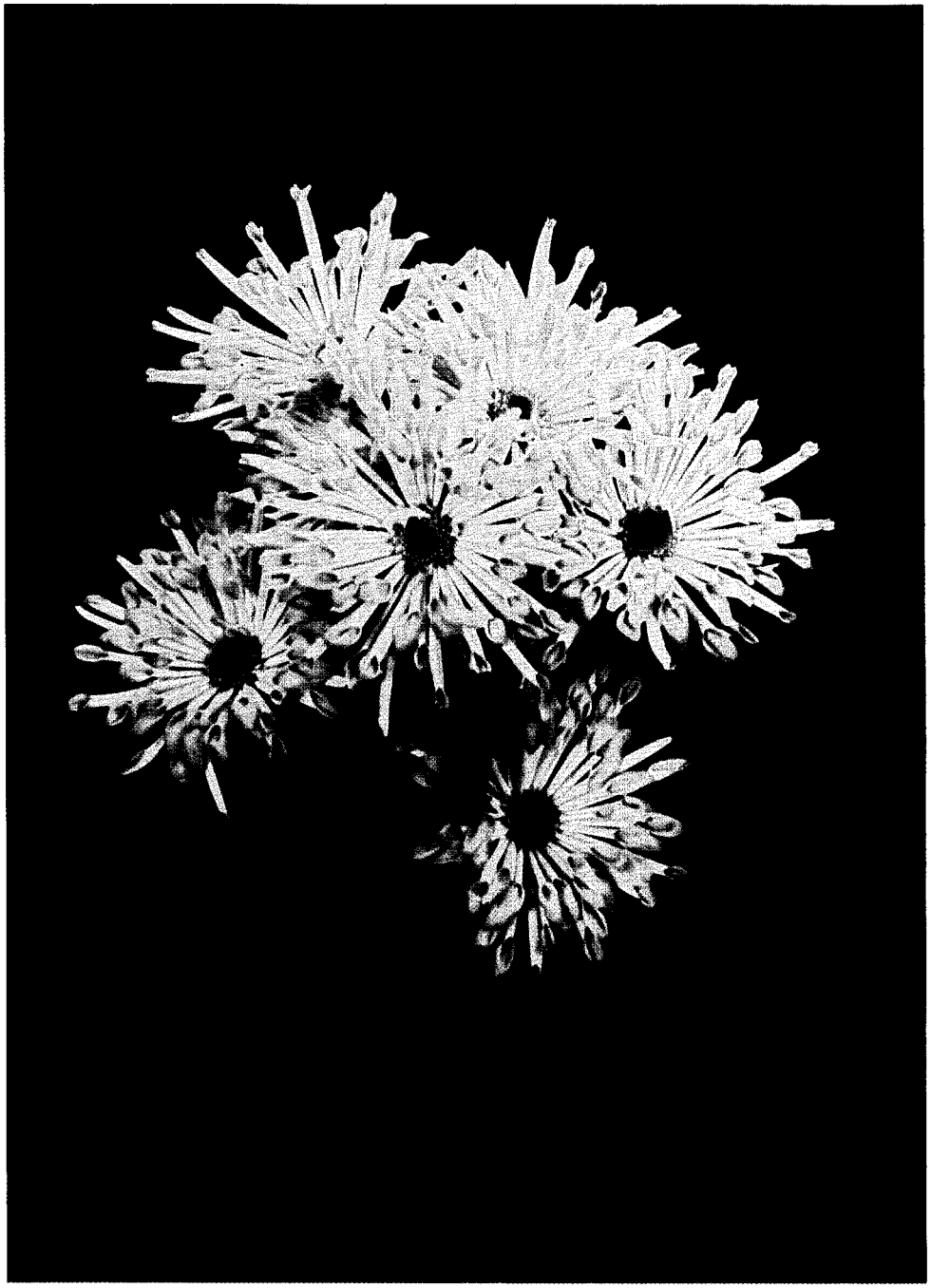

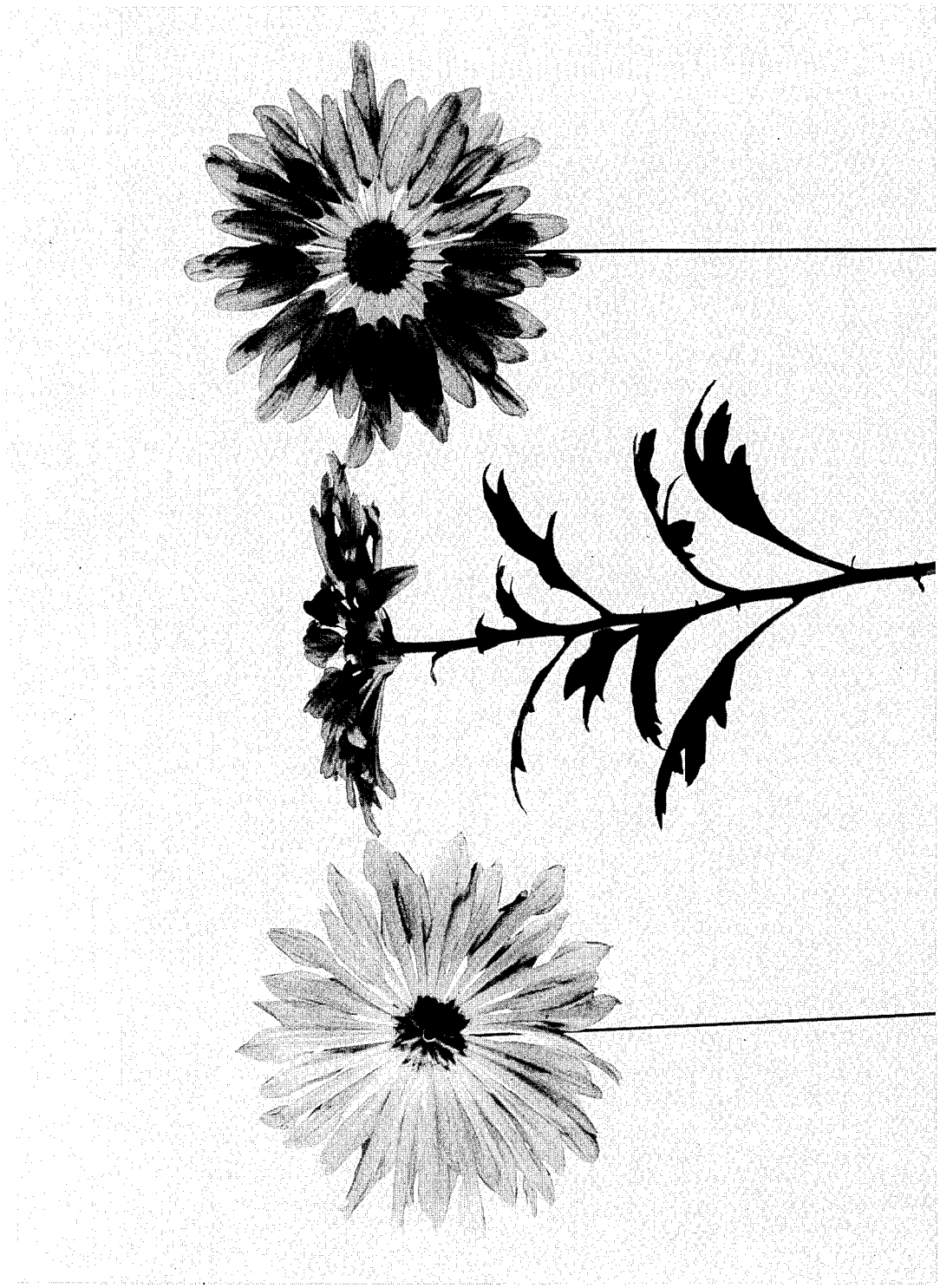

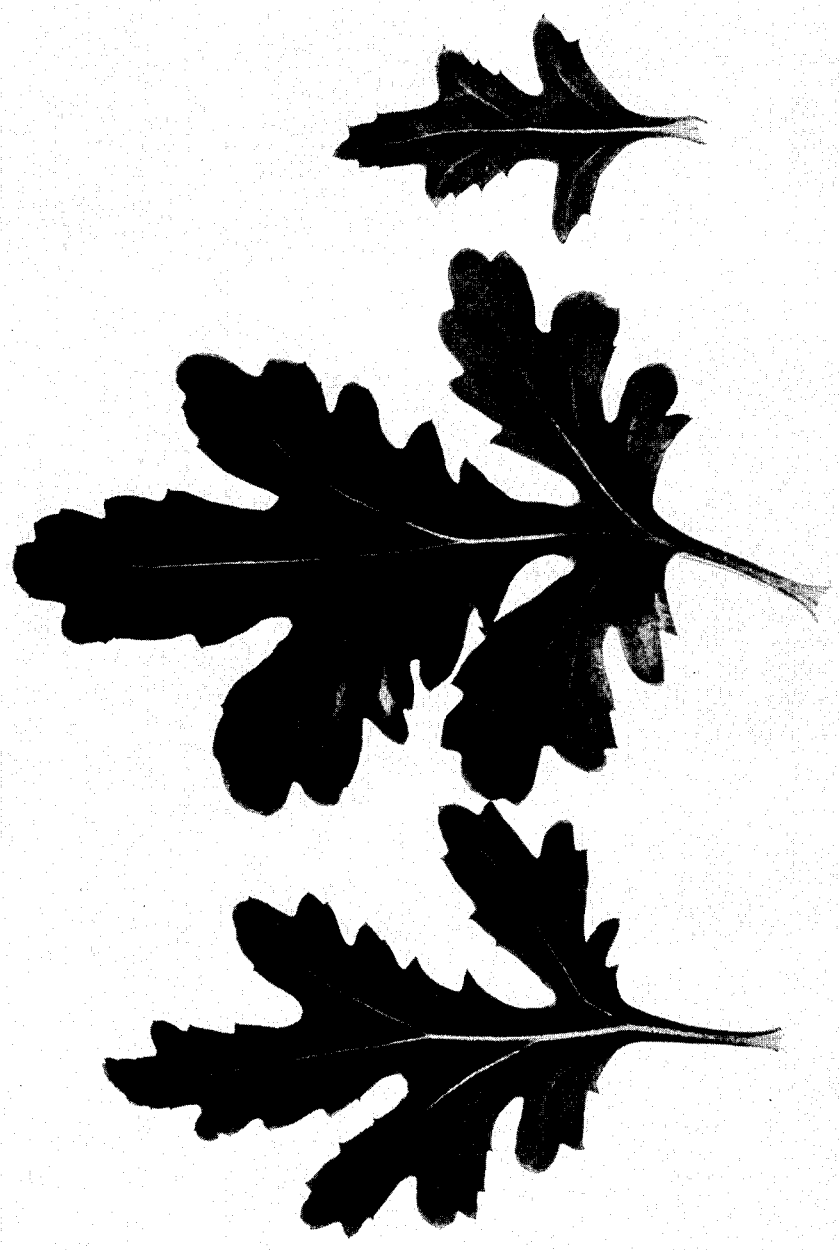

* * * * *